United States Patent [19]

Willer et al.

[11] Patent Number: 5,232,526
[45] Date of Patent: Aug. 3, 1993

[54] DIETHANOLAMMONIUMMETHYLCUBANE NITRATES HYDROXYLAMMONIUM NITRATE (HAN) SOLUTIONS AS AQUEOUS LIQUID GUN PROPELLANT INGREDIENTS

[75] Inventors: Rodney L. Willer, Newark, Del.; Alfred G. Stern, Elkton, Md.

[73] Assignee: Thiokol Corporation, Ogden, Utah

[21] Appl. No.: 911,937

[22] Filed: Jul. 10, 1992

[51] Int. Cl.$^5$ .................. C06B 31/00; C07C 101/44
[52] U.S. Cl. ........................... 149/45; 149/92; 564/456; 564/458; 564/461
[58] Field of Search .............. 149/45, 92; 564/456, 564/458, 461

[56] References Cited

U.S. PATENT DOCUMENTS

| | | | |
|---|---|---|---|
| 3,558,704 | 1/1971 | Gregory | 564/456 |
| 4,402,775 | 9/1983 | Wood | 149/49 |
| 4,527,389 | 7/1985 | Biddle et al. | 149/45 |
| 4,878,968 | 11/1989 | Willer et al. | 149/45 |
| 4,943,302 | 7/1990 | Eaton et al. | 44/56 |
| 5,016,517 | 5/1991 | Pate | 89/7 |

*Primary Examiner*—Edward A. Miller
*Attorney, Agent, or Firm*—Kevin E. Joyce; Ronald L. Lyons

[57] ABSTRACT

This invention is for new compounds, namely, diethanolammoniummethylcubane nitrates, a composition of diethanolammonium methylcubyl nitrates - hydroxylammonium nitrate (HAN) solutions and their method of use as aqueous liquid gun propellant ingredients.

4 Claims, No Drawings

DIETHANOLAMMONIUMMETHYLCUBANE NITRATES HYDROXYLAMMONIUM NITRATE (HAN) SOLUTIONS AS AQUEOUS LIQUID GUN PROPELLANT INGREDIENTS

BACKGROUND AD FIELD OF THE INVENTION

This invention is related to the new compounds, diethanolammonium methylcubyl nitrates, and those compounds in hydroxylammonium nitrate (HAN) solutions as aqueous liquid gun propellants.

Other cubane based fuels are disclosed in "Cubylammonium Nitrate Fuels for Hydroxylammonium Nitrate (HAN) Based Liquid Propellants", Klein, N.; Leverit, C. S.; Willer, R. L.; Cunkle, G. T.; CPIA Publication 498, Vol. 4, pp. 143-147, October, 1988; and references cited there; "Cubanes as Solid Propellant Ingredients", Cunkle, G. T.; Willer, R. L.; Symposium on Innovative Science and Technology Bellingham, Washington, Jan. 10-15, 1988, and U.S. Pat. No. 4,878,968, hereby incorporated by reference in toto, and for pharmaceuticals in U.S. Pat. No. 3,448,368 and 3,558,704.

SUMMARY OF THE INVENTION

This invention is for two new compounds N,N-diethanolammoniummethylcubane nitrate and 1,4 Bis-(N,N-diethanolammoniummethyl)cubane dinitrate.

The invention is also a composition used as a liquid gun propellant comprising an effective amount of hydroxylammonium nitrate, dissolved in an effective amount of water, along with an effective amount of at least one compound selected from the group consisting of N,N-diethanolammoniummethylcubane nitrate and 1, 4-Bis-(N,N,-diethanolammoniummethyl)cubane dinitrate. It is preferred that the hydroxylammonium nitrate be present in an amount of from between about 40 and about 80% by weight, and that water be present in an amount from between about 10 and about 25% by weight. The above named cubyl ammonium nitrates should also be present in an amount of from between about 10 and 25% by weight. "By weight" herein means the total weight of the above ingredients.

This invention is also a method to improve impetus and solubility in liquid gun propellants comprising mixing water with an effective amount of hydroxylammonium nitrate and an effective amount of at least one compound selected from the group consisting of N,N-diethanolammoniummethylcubane nitrate and 1,4-Bis-(N,N-diethanolammoniummethyl) cubyl dinitrate.

DESCRIPTION OF PREFERRED EMBODIMENTS

The use of diethanolammoniummethylcubane nitrates as a co-ingredient in aqueous hydroxyl ammonium nitrate (HAN) solution substantially increases the impetus (Table 1) and solubility of cubylammonium nitrate based liquid gun propellants. Moreover, cubyldiethanolammoniummethyl nitrate shows excellent solubility in HAN solution with only 11.2% $H_2O$ at $-22°$ C. while the corresponding bis compound is soluble in HAN solution with 20% $H_2O$ at-22° C. The preparation of these compounds is shown below. The reactions described are shown graphically following the text.

TABLE 1

BLAKE Calculations* of Candidate Propellant Mixtures

| Mixture | HAN | Fuel | Water | Impetus |
|---|---|---|---|---|
| | (weight percent) | | | |
| HAN-TEAN | 60.8 | 19.2 | 20 | 935.9 |
| HAN-CAN | 66.1 | 13.9 | 20 | 986.0 |
| HAN-CDAN | 59.8 | 20.2 | 20 | 1013.0 |
| HAN-CUN1** | 65.03 | 14.97 | 20 | 948.5 |
| HAN-CUN2** | 67.18 | 12.82 | 20 | 962.3 |

Loading density 0.2 g/cc
TEAN - Triethanolammonium Nitrate (standard LGP Fuel)
CUN1 - cubyl-bis-(1,4-diethanolammonium methyl nitrate)
CUN2 - cubyl-diethanolammonium methyl nitrate
CAN - cubyl ammonium nitrate
CDAN - cubyl bis-1,4 diammonium Dinitrate
*Freedman, E., "BLAKE—A Thermodynamics code Based on TIGER: Users' Guide and Manual," U.S. Army Ballistic Research Laboratory, Aberdeen Proving Cround, MD, Rept. ARBRL-TR-02411, 1982. A calculation to determine the impetus of propellant formulations. The derived impetus is based on the number and type of bonds broken and formed in combustion.
**Examples of this invention, all others are comparative examples.

Following is a description of the method of preparation of the compounds of this invention.

N,N-diethanolaminocarbonylcubane

A mixture of methoxycarbonylcubane (3.0 g, 18 mmol) and diethanolamine (3.1 g, 29.6 mmol, Fisher) was heated at 100° C. for 18 hours under $N_2$. The reaction mixture was allowed to cool to room temperature, was dissolved in methanol (ca. 200 mL), and was filtered through a fritted funnel containing silica gel (ca. 30 g). The solvent was evaporated in vacuo affording a brown solid (4.6 g). Column chromotography (silica gel, isopropyl alcohol) provided the amide (13.7 g, 84.9%) as yellow crystals. DCS (mp 121.4° C.; exotherm 249.8° C.; 1204 J/g). Recrystallization from a minimum quantity of $CHCl_3$ provided an analytical sample of the amide in white crystals. DSC (mp 122–125.3° C., exotherm 250.0° C., 968 J/g). IR (RBr) 3368 (s), 3307 (s), 2983 (s), 1607 (s), 1472 (s), 1070 (s) $cm^{-1}$. $^1H$-NMR (400 MHz, $CHCl_3$) δ4.30 (m, 3 H), 4.13 (s, 1 H), 4.00 (m, 5 H), 3.86 (t, 32 H, J=4.8 Hz), 3.77 (t, 2 H, J=4.8 Hz), 3.52 (t, 2 H, J=4.8 Hz), (t, 2 H, J=4.8 Hz). MS (VG - 70S) EI (70 eV, relative intensity) m/e 234 (m-1, 2.8%), 103 (100%). CI ($NH_3$ 70 eV), m/e 236 (M+1, 100%).

N,N-diethanolaminomethylcubane

Solid N,N-diethanolaminocarbonylcubane (1.00 g, 4.25 mmol) was slowly added to a rapidly stirred suspension of lithium aluminum hydride (0.51 g, 12.75 mmol, Alfa, 95%) in anhydrous tetrahydrofuran (THF, 50 mL) under $N_2$ at room temperature. The mixture as heated to 70° C. and allowed to reflux for 14 hours. The reaction mixture was allowed to cool to room temperature and was quenched by slow sequential addition of distilled $H_2O$ (1.53 mL). The mixture was allowed to stir for 30 min. at room temperature and was filtered. The filter cake was washed with THF (ca. 3×25 mL). The combined THF filtrates were evaporated under vacuum to afford the amine (0.93 g, 99%) as a light yellow oil. IR (NaCl) 3355(m), 2973(s), 2876(m), 1444(w), 1031(s) $cm^{-1}$. $^1H$-NMR (60 MHz, $CDCl_3$) δ4.00 (broad s, 7 H), 3.78–3.48 (m, 6 H), 2.78 (pseudo t, 4 H), 2.52 (s, 2 H). Since the amine trended to colorize it was converted directly to its nitrate salt.

N,N-diethanolammoniummethylcubane Nitrate

A solution of concentrated nitric acid (2.68 mL, 4.25 mmol, Mallinckrodt, 70.7%) and deionized $H_2O$ (0.27 mL) was added to N,N-diethanolaminomethyl cubane (930 mg, 4.20 mmol). Additional deionized $H_2O$ (ca. 14 mL) was added to complete the solution. The cloudy mixture was passed through a fiberglass filter and the filtrate was evaporated in vacuo affording a yellow glass (990 mg, 83%). This material was dissolved in deionized $H_2O$ (50 mL) and treated with neutral Norit (ca 100 mg). The mixture was heated to ca. 60° C. and was filtered. The filtrate was evaporated in vacuo affording the nitrate salt (990 mg, 83%) as a colorless, amorphous solid. DSC (mp 58° C., exotherm 236.6° C., 1951 J/g). IR (KBr) 3405(s), 3233(s), 3183(s), 2977(s) 2976(s), 1380(s) $cm^{-1}$. $^1$H-NMR (400 MHz, $CD_3OD$) δ4.02 (m, 7 H), 3.89 (m, 4 H), 3.58 (s, 2 H), 3.36 (br. s, 4 H).

Preparation of N,N-diethanolammonium Methylcubane Nitrate-Hydroxylammonium Nitrate Solution

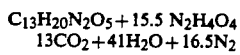

$$C_{13}H_{20}N_2O_5 + 15.5\ N_2H_4O_4$$
$$13CO_2 + 41H_2O + 16.5N_2$$

A concentrated aqueous solution of hydroxylammonium nitrate (123.4 mg, 1.12 mmol, 87%) was added to solid N,N-diethanolammoniummethylcubyl nitrate (20.5 mg, 0.07 mmol) at room temperature. The resultant colorless solution (total $H_2O = 11.2$% by wt.) was placed in a freezer at $-22°$ C. and after 48 hours no precipitate had formed.

1,4-Bis(N,N-diethanolaminocarbonyl)cubane

A mixture of 1,4-dimethoxycarbonylcarboxy cubane (2.2 g, 10.0 mmol) and diethanolamine (5.15 g, 9.1 mmol) was heated at 100° C. for 15 hours under $N_2$. The resultant light brown solid was dissolved in methanol (ca. 100 mL) and the solution was cooled to 0° C. A crystalline solid was collected via filtration, was washed with cold methanol, and was dried to afford bis amide (4.0 g, 80%) as colorless crystals. DSC (mp 191° C.; exotherm 252° C., 797 J/g).

An analytical sample of bis amide was obtained by recrystallization from a minimum quantity of methanol. DSC (mp 191° C., exotherm 252.0° C., 795 J/g). IR (KBr 3456(m), 3381(m), 2943(w), 2864(w), 1583(s), 1482(m), 1436 (m), 1071(m) $cm^{-1}$. $^1$H-NMR (60 MHz, $d_6$-DMSO) δ4.80 (m, 4 H), 4.17 (s, 6 H), 3.40 (m, 16 H). Analysis Calculated for $C_{18}H_{26}N_2O_6$: C, 59.00; H, 7.15; N, 7.65. Found: C, 59.03; H, 7.16, N, 7.61.

1,4-Bis(N,N-diethanolaminomethyl)cubane

Solid 1,4 bis(N,N-diethanolaminocarbonyl)cubane (500 mg, 1.37 mmol) was slowly added to a rapidly stirred suspension of lithium aluminum hydride (328 mg, 8.22 mmol, Alfa, 95%) in anhydrous THF (20 mL) under $N_2$ at room temperature. The mixture was heated to 70° C. and allowed to reflux under $N_2$ for 14 hours. The reaction mixture was allowed to cool to room temperature and was quenched by slow sequential addition of distilled $H_2O$ (0.33 mL), 15% aqueous NaOH(0.33 mL), and distilled $H_2O$ (1.00 mL). The mixture was allowed to stir for 30 min. at room temperature and was filtered. The filter cake was washed with methanol (ca. 75 ml). The combined filtrates were evaporated in vacuo to give crude white solid fritted funnel containing silica gel (ca. 2 gm). The silica gel was washed with additional methanol (10 mL) and the combined filtrates were evaporated in vacuo affording bis amine (440 mg, 95%) as a white solid which darkened on standing. IR (KBr) 3230(m), 2887(s), 2831(s), 1550(s), 1426(s), 1069(s) $cm^{-1}$. $^1$H-NMR (60 MHz, $D_2O$) δ4.15 (s, 6 H), 3.95 (s, 4 H), 3.49 (m, 16 H), 2.63 (t, J=4Hz, 4 H). Since the bis amine tended to colorize it was converted directly to its bis nitrate salt.

1,4 Bis-(N,N-diethanolammoniummethyl)cubyl Dinitrate

A solution of concentrated nitric acid (0.35 mL, 5.53 mmol, Mallinckrodt, 70.7%) in deionized $H_2O$ (0.35 mL) was added to 1,4-Bis(N,N-diethanolaminomethyl)cubane (927 mg, 2.74 mmol). Additional deionized $H_2O$ (2 mL) was added to complete the solution. The cloudy mixture was passed through a fiberglass filter and the filtrate evaporated in vacuo to afford the dinitrate salt (1.15 g, 91%) as an off-white solid. This was dissolved in deionized $H_2O$ (ca. 30 ml) and treated with neutral Norit (ca. 150 mg). The mixture was heated to ca. 60° C. and was filtered. The filtrate was evaporated in vacuo affording the salt (1.09 g, 86%) as a colorless solid.

Recrystallization from a minimum quantity of Reagent alcohol (90 EtOH: 5% i-PrOH: 5% MeOH, Fisher) gave the salt as color less crystals. DSC (mp 66°-69° C., exotherm 192.9° C.; 829 J/g). IR (KBr) 3370(s), 2964(m), 1382(s), 1051(m) $cm^{-1}$. $^1$H-NMR (400 MHz, $D_2O$) δ4.32 (m, 4 H), 4.14 (s, 6 H), 3.76 (m, 5 H), 3.67 (br.s, 1 H), 3.61 (br.s, 2 H), 3.46–3.24 (br. m, 6 H), 3.20 (m, 6 H).

Preparation of 1,4 Bis(N,N-diethanolammoniummethyl)cubyl dinitrate-hydroxylammonium Nitrate Solution

$$C_{18}H_{32}N_4O_{10} + 2N_2H_4O_4\ \ 18CO_2 + 58H_2O + 23N_2$$

Solid 1,4-bis-(N,N-diethanolammoniummethyl)cubyl dinitrate (12.2 mg, 0.026 mmol) was added to a concentrated aqueous solution of hydroxylammonium nitrate (60.9 mg, 0.552 mmol, 87%) at room temperature. The mixture was shaken for ca. 18 hours and deionized $H_2O$ (6 μl, 0.333 mmol) was added and the mixture was heated to ca. 37° C. The resultant solution was placed in a freezer at $-22°$ C. and after 30 min. a precipitate had formed. The solution was diluted with additional deionized $H_2O$ (2 μl, 0.111 mmol) and the resultant solution was again cooled to $-22°$ C. A small amount of precipitate was observed after the solution was allowed to stand for 20 hours at $-22°$ C. Additional deionized $H_2O$ (0.4 μl, 0.009 mmol) was added to complete the solution (total $H_2O = 20$% by wt.). No precipitate was observed after 18 hours at $-22°$ C.

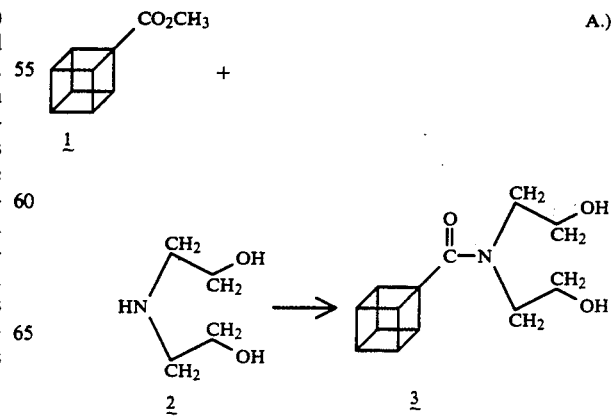

-continued

B.) 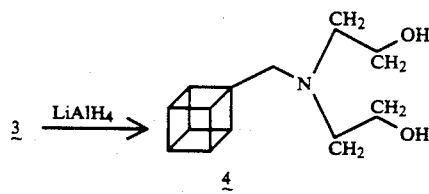

C.) 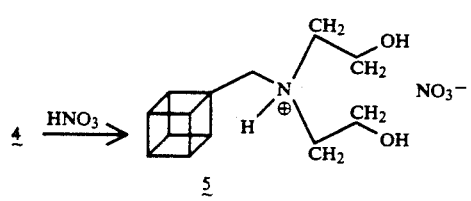

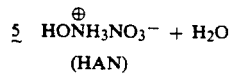 + H₂O
(HAN)

E.) 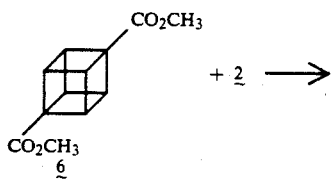

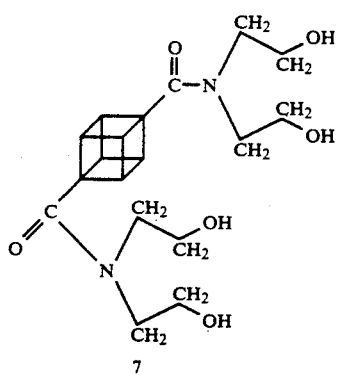

-continued

F.) 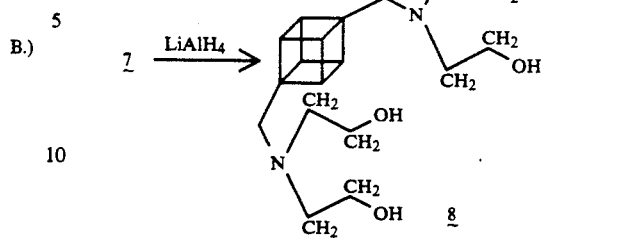

G.) 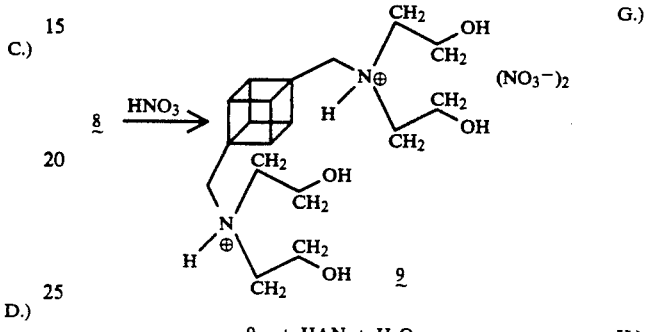

H.) 9 + HAN + H₂O

While the invention has been described in connection with what is presently considered to be the most practical and preferred embodiments, the invention is not limited to the disclosed embodiment but, on the contrary, is intended to cover various modifications and equivalents included within the spirit and scope of the following claims.

What is claimed is:

1. N,N-diethanolammoniummethylcubane nitrate.
2. 1,4Bis-(N,N-diethanolammoniummethyl)cubane dinitrate.
3. A composition useful as a liquid gun propellant comprising:
   a) an effective amount of hydroxylammonium nitrate, dissolved in an effective amount of water, along with
   b) an effective amount of at least one compound selected from the group consisting of N,N-diethanolammoniummethylcubane nitrate and 1,4 Bis-(N,N-diethanolammoniummethyl)cubane dinitrate.
4. The composition of claim 3, wherein compound a) is present in an amount of from between about 40 and about 30 percent by weight, water is present in an amount of from between about 10 and 25 percent by weight, and compound b) including mixtures thereof, is present in an amount of from between about 10 and 25 percent by weight.